US011439527B2

(12) United States Patent
Matthews (10) Patent No.: US 11,439,527 B2
(45) Date of Patent: Sep. 13, 2022

(54) ORTHOTIC DEVICE AND METHOD OF MAKING AN ORTHOTIC DEVICE

(75) Inventor: Martin Matthews, Redruth (GB)

(73) Assignee: DM ORTHOTICS LIMITED

(*) Notice: Subject to any disclaimer, the term of this patent is extended or adjusted under 35 U.S.C. 154(b) by 425 days.

(21) Appl. No.: 14/004,118

(22) PCT Filed: Mar. 12, 2012

(86) PCT No.: PCT/GB2012/050543
§ 371 (c)(1),
(2), (4) Date: May 15, 2014

(87) PCT Pub. No.: WO2012/120316
PCT Pub. Date: Sep. 13, 2012

(65) Prior Publication Data
US 2014/0296759 A1 Oct. 2, 2014

(30) Foreign Application Priority Data
Mar. 10, 2011 (GB) ..................................... 1104074

(51) Int. Cl.
*A61F 5/02* (2006.01)
(52) U.S. Cl.
CPC ................ *A61F 5/026* (2013.01); *A61F 5/02* (2013.01); *A61F 5/024* (2013.01)
(58) Field of Classification Search
CPC .......... A61F 5/026; A61F 5/024; A61F 5/022; A61F 5/028; A61F 5/03; A61F 5/32;
(Continued)

(56) References Cited

U.S. PATENT DOCUMENTS 4,216,547 A * 8/1980 Picchione .......... A41D 13/0543
2/22
4,285,336 A 8/1981 Oebser et al.
(Continued)

FOREIGN PATENT DOCUMENTS

CN 2706141 6/2005
DE 20009763 8/2000
(Continued)

OTHER PUBLICATIONS

Prosthetics and Orthotics International "The Use of Dynamic Lycra Orthosis in the Treatment of Scoliosis: A Case Study"; 8 pages; M. Matthews and R. Crawford; Aug. 2006.
(Continued)

*Primary Examiner* — Michelle J Lee
(74) *Attorney, Agent, or Firm* — Gardner Groff & Greenwald, PC (57) ABSTRACT

An orthotic device (10) that may be particularly effective in the treatment of scoliosis comprises a torso section (20) and a resilient reinforcement (40) attached to the torso section. The reinforcement extends diagonally across a front and/or a rear portion of the torso section between a first attachment point (51) at a first side of the torso section and a second attachment point (52) at a second side of the torso section. At least one of the first attachment point and the second attachment point is locally indented into the torso section such that the reinforcement is stretched when device is donned a patient, thereby applying a force to the patient's torso.

18 Claims, 3 Drawing Sheets

(58) Field of Classification Search
CPC ............. A61F 5/02–03; A61F 5/30–37; A41D 13/00–08; A41D 1/00–22; A41D 1/22; A41D 2400/00; A41D 2400/80; A41D 2400/82; A41D 13/05; A41D 13/0506; A41D 1/067; A41D 13/0518–0531; A41D 13/0531; A41D 13/0007; A41D 13/055; A41D 13/0556; A41D 13/0568; A41D 2400/32; A41D 2400/322; A41D 2400/38; A41C 1/08; A41C 1/00; A41C 1/02–10; A41C 1/10; A41B 9/00; A41B 9/08
See application file for complete search history.

(56) References Cited

U.S. PATENT DOCUMENTS

| | | | |
|---|---|---|---|
| 4,688,558 A | | 8/1987 | Hooper, Jr. et al. |
| 4,698,847 A | * | 10/1987 | Yoshihara ................ A41C 1/06 450/7 |
| 5,109,546 A | * | 5/1992 | Dicker ............... A63B 21/4025 2/70 |
| 5,256,135 A | | 10/1993 | Avihod |
| 5,474,523 A | | 12/1995 | Miller |
| 5,599,286 A | | 2/1997 | Labelle et al. |
| 5,710,160 A | | 1/1998 | Guay et al. |
| 5,816,251 A | | 10/1998 | Glisan |
| 6,440,094 B1 | | 8/2002 | Maas |
| D571,016 S | | 6/2008 | Matthews |
| 8,287,478 B2 | * | 10/2012 | Ostergard ............. A61F 5/3723 2/45 |
| 8,533,864 B1 | * | 9/2013 | Kostrzewski ........ A41D 31/185 2/69 |
| 9,452,074 B2 | * | 9/2016 | Wynne ..................... A61F 5/03 |
| 2003/0130603 A1 | | 7/2003 | Minne |
| 2005/0197607 A1 | * | 9/2005 | Brown ................. A61F 5/3746 602/19 |
| 2008/0040831 A1 | * | 2/2008 | Nilforushan ....... A41D 13/0058 2/69 |
| 2009/0275871 A1 | * | 11/2009 | Liu ........................... A61F 5/34 602/19 |
| 2010/0217166 A1 | * | 8/2010 | Mills ...................... A61F 5/024 602/19 |

FOREIGN PATENT DOCUMENTS

| | | | | |
|---|---|---|---|---|
| DE | 102006021321 | | 11/2007 | |
| DE | 102010000189 | | 7/2011 | |
| DE | 102010000189 A1 | * | 7/2011 | ............... A61F 5/01 |
| DE | 102010000189 A1 | * | 7/2011 | ............... A61F 5/01 |
| ES | 2294590 | | 4/2008 | |
| JP | 2009035838 | | 2/2009 | |
| JP | 3173281 | | 2/2012 | |
| KR | 20100089953 | | 8/2010 | |
| WO | 9312739 | | 7/1993 | |
| WO | 9517142 | | 6/1995 | |
| WO | 2005023157 | | 3/2005 | |

OTHER PUBLICATIONS

International Search Report for PCT/GB2012/050543 dated Jul. 10, 2012.
Intellectual Property Office Search Report for Application No. GB1104074.8 dated Mar. 5, 2012.
Notice of Reasons for Rejection for Application No. 2013-557178, dated Dec. 22, 2015, 7 pages.
Chinese Search Report for Application No. 201280022646.9 dated Dec. 3, 2014.
Examiner's Report from the Brazilian Patent and Trademark Office, dated Sep. 18, 2019.
Chinese Text of the Second OA in counterpart Chinese Application No. 201610875453.8, dated Jun. 17, 2019.
English Translation of the Second OA in counterpart Chinese Application No. 201610875453.8, dated Jun. 17, 2019.

* cited by examiner

FRONT VIEW          BACK VIEW

FIG. 3

FRONT VIEW          BACK VIEW

FIG. 4

ORTHOTIC DEVICE AND METHOD OF MAKING AN ORTHOTIC DEVICE

CROSS-REFERENCE TO RELATED APPLICATION

This is a national-phase filing of PCT International Patent Application Serial No. PCT/GB2012/050543, filed Mar. 12, 2012, which claims the priority benefit of Great Britain Patent Application Serial No. 1104074.8, filed Mar. 10, 2011, both of which are hereby incorporated herein by reference.

The invention relates to an orthotic device and a method of making an orthotic device. The device may be particularly suitable for use in the treatment of scoliosis.

BACKGROUND OF THE INVENTION

Scoliosis is a condition involving a lateral curvature of the spine, often coupled with vertebral rotation. Untreated scoliosis can cause problems with respiratory and cardiac functions, as well as pain, and restricted mobility and limb functions. The treatment of scoliosis varies depending on the severity of the spinal curvature, and may involve physiotherapy, bracing or, in severe cases, surgery.

A typical non-surgical treatment of scoliosis involves the use of a rigid thoraco-lumbar brace to hold the spine in a preferential position, thereby enabling a wearer to experience improved posture and limb functionality. An example of such a rigid thoracic brace is the Boston brace developed in 1976. Typically, rigid brace treatment involves the wearing of a brace for up to 23 hours in a day. Studies have shown that such treatment may have a positive effect when the brace is worn for the prescribed periods of time. However, compliance with the prescribed treatment regimen may often be poor due to the inconvenience of wearing a rigid brace for long periods of time. Studies have shown that in some cases a brace was only worn 20% of the prescribed time, resulting in the treatment having little effect on prognosis of the scoliosis (Howton et al. 1987 orthopaedic transactions 11: 125-126).

Other methods of bracing have been used in the treatment of scoliosis. For example, the SpineCor brace is a dynamic brace that relies on elastic bands to apply a dynamic corrective force to a patient's trunk to correct spinal curvature. There may be patient comfort issues such as abrasion involved in use of the SpineCor brace, but overall patient compliance appears to be increased compared with a rigid brace system.

Matthews and Crawford (Prosthetics and Orthotics International August 2006; 30(2): 174-181) describe the use of a dynamic elastomeric fabric orthosis consisting of a Lycra® body-suit with the addition of elastomeric panels that act to counter thoracic spine rotation and lateral curvature. Patient compliance and comfort were improved with respect to a rigid brace, and the orthosis did not have the same abrasion issues as the SpineCor dynamic brace. The suit also appeared to provide beneficial proprioceptive effects and the visual appearance of the suit was improved compared with previously known braces. The orthosis described by Matthews and Crawford may be limited in the force that can be provided by the elastomeric panels, however, which may limit the situations in which the suit is applicable.

SUMMARY OF INVENTION

The invention provides an orthotic device and a method of making an orthotic device according to the appended independent claims to which reference should now be made. Preferred and/or advantageous features of the invention are set out in various dependent sub-claims.

Thus, the invention may provide an orthotic device comprising a torso section fabricated from a material for conforming to at least a portion of a wearer's torso and a reinforcement for applying a force to the wearer's torso to urge a portion of the wearer's spine in a substantially lateral direction. The reinforcement comprises resilient material attached to the torso section, preferably in the form of a strip or panel, that extends diagonally across a front portion, and/or a rear portion, of the torso section between a first attachment point at a first side of the torso section and a second attachment point at a second side of the torso section. The first attachment point is locally indented into the first side of the torso section, and/or the second attachment point is locally indented into the second side of the torso section, such that the resilient material attached to the torso section is stretched when the orthotic device is donned by the wearer, thereby applying the force to the wearer's torso.

A resilient material is a material that can elastically deform under load and return to its original shape when the load is removed, for example rubber materials or elastomeric fabric materials.

The material forming the torso section of the device, which may be termed an underlying material, is preferably a resilient or elastomeric material that is capable of conforming to the wearer's body without generating substantial directional forces, or giving rise to lines of tension or compression in any specific direction. Suitable materials are readily available, for example elastomeric materials comprising a polyurethane-polyurea copolymer such as Dorlastan®, Spandex®, or Lycra®. A particularly suitable material may be a polyamide-cotton-Dorlastan® material, for example a material comprising 51% polyamide, 17% cotton and 32% Dorlastan®.

The reinforcement that is attached to the torso section to form the device includes one or more sections of resilient material. The purpose of the resilient material in the reinforcement is to apply a force acting in one or more predetermined directions to assist and/or restrict movement of the wearer's torso. Particularly preferably, the resilient material is in the form of one or more strips or panels of resilient or elastic material that are attached to the torso section to produce a lateral force that acts on the wearer's spine.

It is preferable that the resilient material forming the reinforcement is a different material from the underlying material forming the torso section. For example, the reinforcement may comprise one or more elongated strips or panels of a resilient material such as a nylon/cotton material or a nylon/Lycra® material, for example a material comprising 81% polyamide and 19% Lycra®.

When the device is worn, the reinforcement may provide a constant force to the wearer's torso that urges the wearer's spine in a specific direction. The reinforcement may also provide a force that resists movement of the wearer's torso and spine when the wearer moves their torso in a specific direction.

The torso section is indented at the first attachment point, the second attachment point, or both first and second attachment points. The circumference of the torso section at the indent or the indents is reduced. Thus, when the device is worn, the material at the indents needs to stretch more than the rest of the material in order to conform to the wearer's torso. By stretching when the device is worn, the resilient material is placed under tension. This tension applies a compressive force to the user. The depth of the indent or indents controls the tension that the resilient material is placed under and, thereby, the power of the device.

By attaching the reinforcement to the torso section at one or more indents, the reinforcement material (i.e. the resilient material) may be attached to the first portion in a non-tensioned condition, only becoming tensioned when the device is worn. Thus, the strips or panels of resilient material forming the reinforcement need not have a force applied to them when they are attached to the underlying resilient material of the torso section. It is not easy to pre-tension a resilient material and then attach it to an underlying orthotic device, for example by stitching. It also becomes more difficult to pre-tension a resilient material as the force the material is required to produce increases. By attaching the reinforcement at an indent, these problems may be overcome.

An indent may locally reduce the circumference of the torso section by greater than 2%. Preferably the circumference is reduced by between 3% and 30%, preferably between 5% and 25%, preferably between 7.5% and 20%. The circumference may be reduced by about 10% or about 15%.

The indents cause the reinforcement material to stretch when the device is worn. The reinforcement material preferably stretches by between 2% and 25% of its length, for example between 5% and 20%, or between 10% and 15%. The more the reinforcement stretches, the greater the force exerted by the reinforcement.

It is preferred that one of the first or second attachment points is located level with a patient's hip on one side of the torso section and that the other of the first or second attachment points is located between the hip and the armpit on the other side of the torso section. The reinforcement extends diagonally between the first and second attachment points. For the avoidance of doubt, the assignment of the terms first attachment point, second attachment point, and, where needed, third attachment point, has no bearing on the function of the device. For the purposes of the following discussion, an attachment point that is level with the hip is referred to as the second attachment point and an attachment point located between the hip and the armpit on the opposing side of the torso section to the second attachment point is referred to as the first attachment point. An attachment point located between the hip and the armpit on the same side of the torso section as the second attachment point is referred to as a third attachment point.

While either or both of the first and second attachment points may be locally indented, it is preferred that an attachment point located at the hip, i.e. the second attachment point in the convention adopted for the purposes of this description, is not indented, or is only indented to a small degree compared with the first attachment point. There may be some wearer discomfort if a hip attachment point is locally indented to a great degree.

In preferred embodiments of the orthotic device, the second attachment point is located level with a patient's hip, or at the lowest point on one side of the torso section, and is not locally indented, whereas the first attachment point is located between the hip and armpit on the opposite side of the torso section and is locally indented, Advantageously, the reinforcement may comprise a further section of resilient material extending laterally or diagonally across a front portion, and/or a rear portion, of the torso section between the first attachment point and a third attachment point that is vertically spaced from the second attachment point on the second side of the torso section. The third attachment point may be locally indented relative to the torso section. The reinforcement applies a compressive force that urges a wearer's torso in a lateral direction towards the second side of the torso section.

Where the reinforcement comprises sections of resilient material that attach to a first attachment point on one side of the torso section, and second and third attachment points on a second side of the torso section, the reinforcement may be described as being "V-shaped", although the "V" is on its side when the device is worn. The first attachment point forms the apex of the "V", and the second and third attachment points are at the end of each of the legs of the "V".

Where the reinforcement is "V-shaped" in the front view or rear view (or both) as described above, the first attachment point refers to the point on one side of the torso section that the reinforcement contacts, and the second and third attachment points refer to points on the opposite side of the torso section that the reinforcement contacts. When the resilient material forming the reinforcement is stretched, lines of tension are produced between the first attachment point and the second attachment point and between the first attachment point and the third attachment point.

It is preferable that the reinforcement extends across both front and rear portions of the torso section. Thus, in a preferred configuration the device may have reinforcement material attached at a first attachment point on, say, a left side of the torso section, and at second and third attachment points on a right side of the torso section. Sections of reinforcement material may extend across both the front and rear of the torso section between the first attachment point and the second attachment point and between the first attachment point and the third attachment point. It is preferred that the torso section is indented at the first attachment point, and there may be further indents at one or both of the second and third attachment points. The effect of the indents is to reduce the length of the sections of resilient material that form the reinforcement when the device in not worn. Thus, when the device is worn and the material at the indents is stretched (i.e. both the underlying resilient material and the reinforcement material) the reinforcement material causes a force to be applied to the wearer's torso.

Where the reinforcement is applied to the device in a "V-shape" to the front and/or rear of the torso section, a force is applied to the wearer's torso in a lateral direction from the first attachment point, or apex of the "V", toward the second side of the torso section. Thus, if the first attachment point is on the left side of the device, the lateral force acts in a left to right direction. If the first attachment point is on the right of the device, the lateral force acts in a right to left direction.

It is preferred that the second attachment point is fixed to be level with a patient's hip on either the left side or right side, as required. The first attachment point may be located at any point above the hip on the opposite side to the second attachment point, as determined by a medical practitioner. By moving the location of the first attachment point vertically up or down, the point at which the lateral force has maximum effect may be moved up or down. Scoliosis may result from curvature low in the spinal column or high in the spinal column. Typically the curvature will result in a "C-shape" to the spine when viewed from the rear. A double curvature may also cause an "S-shape" in the spine when viewed from the rear. By moving the first attachment point up or down, the device may be tailored to provide a corrective force at the appropriate point for a particular patient.

Preferably, the position of the first attachment point is determined by reference to an x-ray of the wearer's spine. Such an x-ray will show the position and extent of the scoliotic curve and allow the first attachment point to be chosen for most effective treatment. The process of preparing an orthotic device using x-ray information is known as x-ray blueprinting.

The height of the third attachment point may also be determined by x-ray blueprinting. Preferably the second attachment point, however, is determined by the position of the wearer's hip, i.e. without reference to the patient's condition.

Typically scoliosis patients have a lateral curvature of the spine of between 10 degrees and 60 degrees or more. A low degree of scoliosis may not require a high applied force for treatment, whereas a more severe scoliosis may require treatment using an orthotic device that exerts a greater corrective force. The use of indents at attachment points for the reinforcement provides a simple means to tailor the corrective force provided by the device to a patient's needs. A shallow indent means that the reinforcement only needs to stretch a small amount in order for the device to conform to a patient's torso. Thus, the elastic force urging the reinforcement back towards its un-stretched state is low, and the corrective force transmitted to the patient is correspondingly low. By forming a device with an increased indent, the corrective force applied to the patient may be increased. In combination with the selection of different resilient materials having different degrees of elasticity to form the reinforcement, the corrective force transmitted to a patient may be carefully controlled to provide appropriate treatment.

An orthotic device according to embodiments of the invention may comprise additional reinforcement panels to exert forces in other directions to those described above. For example, the device may additionally comprise a reinforcement consisting of a section of a resilient material that extends from a central point on a front side of the torso section to a centre point on a rear side of the torso section. Such a reinforcement panel is preferably situated on the side of the wearer's body at which the spinal curve is convex and may provide a resistance to the curve via the wearer's thoracic cage.

In a further example of an optional reinforcement panel, embodiments of an orthotic device may comprise a section of reinforcement material that acts as a reinforcement to counter thoracic spine rotation. Such reinforcement may be termed spinal de-rotation reinforcement.

In a first configuration, a spinal de-rotation reinforcement may comprise a strip of resilient material that has a first end located on the torso section at an anterior portion of a shoulder. In most circumstances, the shoulder is the shoulder located on the same side of the torso section as the first attachment point described above. In some unusual circumstances, the shoulder may be on the opposite side of the torso section as the first attachment point. The strip of material extends over the shoulder and then downwards until clear of the axilla area. The strip then extends diagonally across the front of the chest and terminates at a second end located at a portion of the torso section near to the anterior superior iliac spine, i.e. near the hip. The second end is at approximately the same location as the second location point described above.

In a second configuration, a spinal de-rotation reinforcement may comprise a strip of resilient material that has a first end located on the torso section at an posterior portion of a shoulder. The shoulder is the shoulder located on the same side of the torso section as the first attachment point described above. The strip of material extends over the shoulder and then downwards until clear of the axilla area. The strip then extends diagonally across the rear of the torso section and terminates at a second end located at a portion of the torso section near to the anterior superior iliac spine, i.e. near the hip. The second end is at approximately the same location as the second location point described above.

The strip of resilient material may be any suitable material, and may be multiple strips of material. The action of a spinal de-rotation reinforcement is to compress the convex side of the spinal curvature in a patient suffering from scoliosis, thus countering the natural progression of the scoliotic curve rotation, and to provide either a posterior or anterior acting force on the shoulder.

The orthotic device may take the form of a vest. The device may, however, be in the form of a body suit. In this case the device may have arm sections and leg sections in addition to the torso section. Leg sections may assist the anchoring of a lower portion of the device so that the attachment points do not stray from their intended position with respect to the wearer.

Fasteners such as zips may cut through reinforcement materials. The functionality of the reinforcement material, i.e. a strip or panel of a resilient material, should not be affected as long as a secure attachment is made on either side of the fastener. Forces generated by the reinforcement are transmitted through the fastener when it is closed. It is preferred that the fastener is a zip fastener.

The invention may also provide a method of making an orthotic device as described above comprising the steps of determining the vertical position of the first attachment point based on x-rays of the wearer's torso (blueprinting), producing a torso section for substantially-conforming to the wearer's body, the torso section being indented at the first attachment point, and attaching the reinforcement means to the torso section such that it is stretched when worn by the wearer. Advantageously, the reinforcement material is attached in an un-stretched condition. It is preferred that the location of the second attachment point is determined by the position of a patient's hip.

The method may involve a further step of determining the corrective force desired from the device and selecting the reinforcement material and/or the indent depth to achieve this force.

In one aspect the invention may provide an orthotic device comprising a torso section fabricated from a material for conforming to at least a portion of a wearer's torso and reinforcement for applying a force to a first shoulder of the wearer to provide a posterior or anterior acting force on the shoulder. The reinforcement comprises resilient material attached to the torso section, preferably in the form of a strip or panel. The resilient material extends upwardly from an anterior or posterior shoulder position on a first side of the torso section, upwardly over the first shoulder and then downward over the shoulder-blade until clear of the axilla. The resilient material then extends diagonally downwards across the front or rear of the torso section and is attached to the torso section at a position approximately at the anterior superior iliac spine or upper trochanter (i.e. at the hip) on a second side of the torso section opposite the first side of the torso section. The orthotic device comprises an arm section that encapsulates the first shoulder. The arm section may extend as required, and preferably covers at least an upper portion of the arm. There is no arm section on extending from the second side of the torso section. This orthotic device provides a spinal de-rotation effect, and pulls the first shoulder either backwards and down or forwards and down.

If used on a scoliosis patient, this device is preferably configured such that the first shoulder is the shoulder on the convex side of the patient's scoliosis curve.

The presence of the arm section on the same side as the first shoulder, but not on the side of the second shoulder, provides a counter-rotational force on the first shoulder.

Preferably, the orthotic device includes a pressure relief panel located at a second shoulder of the torso section. The pressure relief panel is a fastenable flap that can be opened to allow the wearer's second shoulder to be free of the orthotic device. The flap may be fastened once the wearer has donned the device.

An orthotic device comprising a spinal de-rotation reinforcement may comprise any other reinforcements described above in relation to other orthotic devices.

SPECIFIC EMBODIMENT OF THE INVENTION

A specific embodiment of the invention will now be described with reference to the figures, in which.

Figure 1:
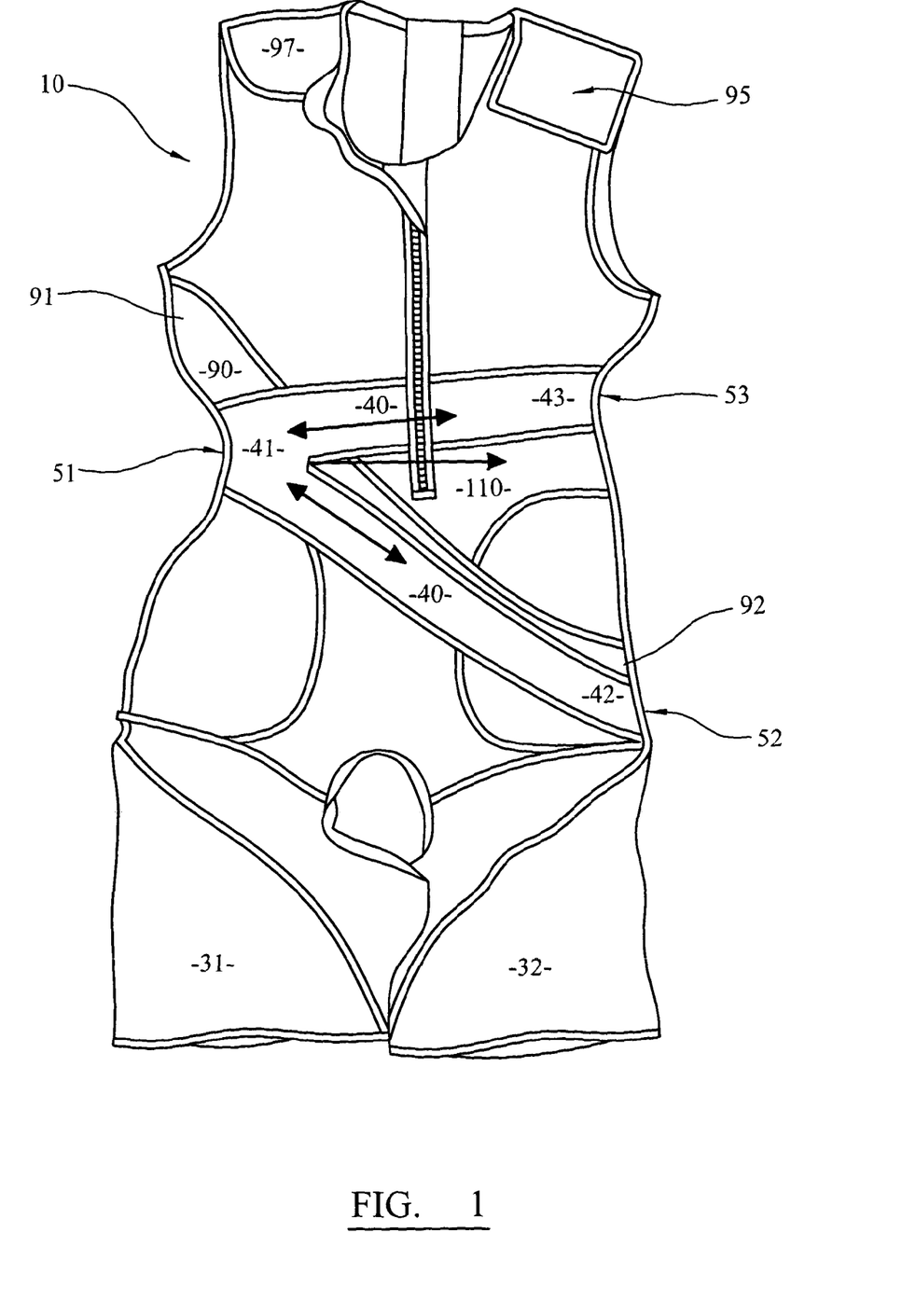
FIG. 1 illustrates a frontal view of an orthotic device according to an embodiment of the invention.

FIG. 1 illustrates an orthotic body-suit 10 for the treatment of scoliosis. The frontal view of the suit is illustrated. The body-suit 10 is an orthotic device and comprises a torso section 20 for covering a wearer's torso and pelvis, and leg sections 31, 32 that extend down an upper portion of a wearer's right and left leg respectively. The torso section 20 and the leg sections 31, 32 are formed from an elastomeric material having a composition of 51 polyamide, 17% cotton and 32% Dorlastan®. This material is a lightweight, breathable, elastomeric fabric and is suitable for forming the underlying material of the body-suit 10. Other suitable fabrics are available, for example under the trade names Spandex® or Lycra®.

The body-suit 10 has a first reinforcement panel 40 that is v-shaped when viewed from the front. This reinforcement panel may also be termed a translatory panel, as it provides a translation force to the wearer's torso. This panel extends from a first attachment point 51 on a right side of the torso section, where the apex of the "V" 41 is attached, to second and third attachment points 52, 53 on a left side of the torso section, where lower and upper portions of the "V" 42, 43 are attached. The first reinforcement panel 40 extends around the rear of the suit in the same way as it extends across the front of the suit. Thus, in a rear view the reinforcement panel would also appear to be v-shaped.

Effectively, the first reinforcement panel provides two bands of reinforcement. A first band encircles the torso section and extends diagonally upwards from the first attachment point 51 to the third attachment point 53, and a second band encircles the torso section and extends diagonally downwards from the first attachment point 51 to the second attachment point 52.

The first reinforcement panel 40 is formed from a resilient material having a composition of 81% polyamide and 19% Lycra®, which is an elastomeric material that offers greater resistance to deformation than the underlying elastomeric material.

The first reinforcement panel 40 is attached to the underlying resilient material of the body-suit by means of stitching. This stitching follows the edges of the panel. Thus, the first reinforcement panel 40 is not only attached to the body-suit at the designated attachment points.

It is noted that the first reinforcement need not be a single v-shaped panel as illustrated in figure one. A plurality of strips of resilient material may be attached to the torso section in order to produce lines of tension between the first attachment point and the second attachment point and between the first attachment point and the third attachment point.

Figure 2:
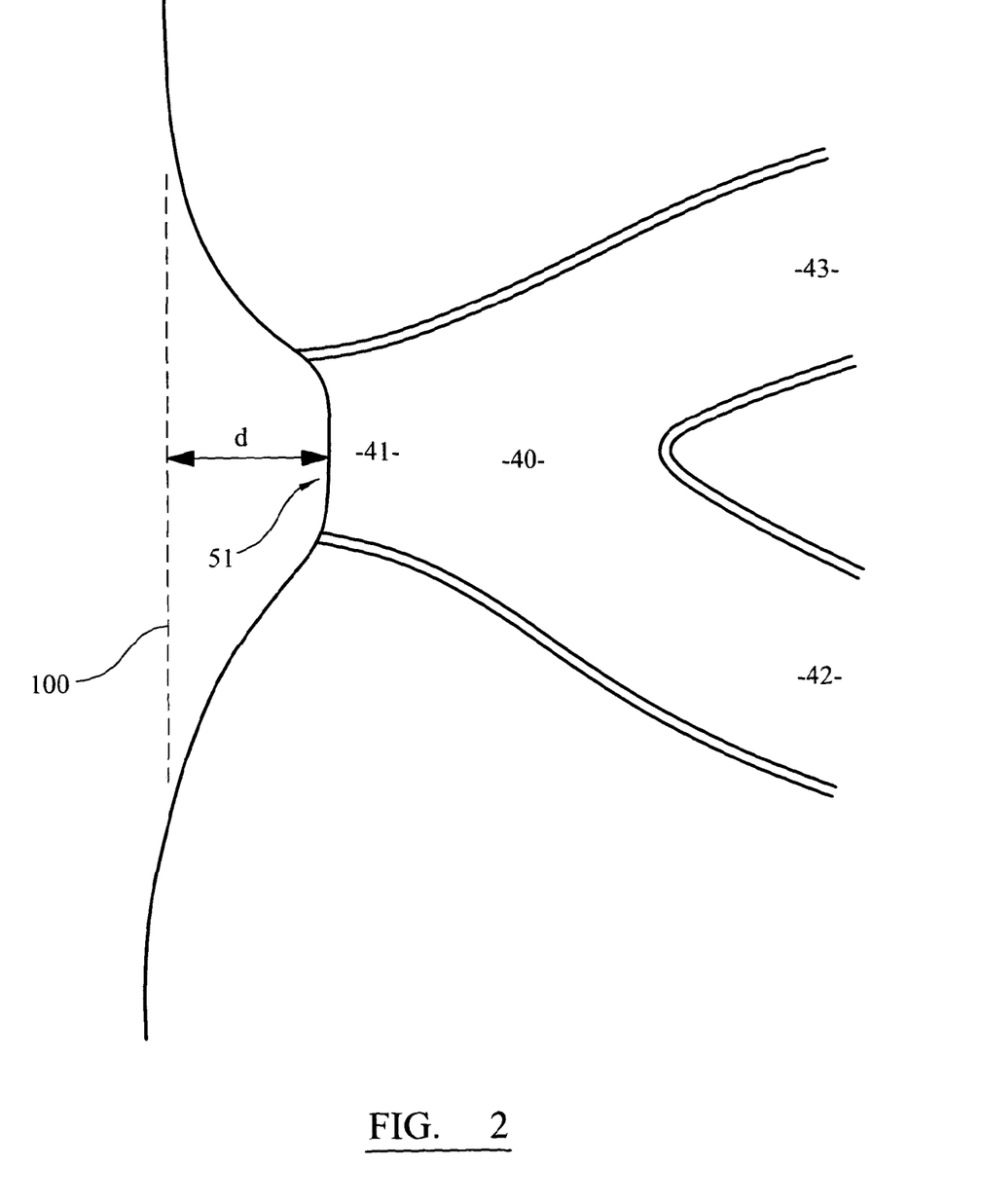
FIG. 2 is a schematic illustration showing the indent in the embodiment as illustrated in FIG. 1.

The first attachment point 51 is indented into the right side of the torso section. This is more clearly illustrated by FIG. 2. In FIG. 2, a dotted line 100 shows the position the right side of the torso section would take if there was no indent. This is also the line that the right side of the torso section has when the device is worn, as the wearer's body stretches the fabric forming the device and eliminates the indents. The depth of the indent may be defined as the distance between the actual position of the material at a point of attachment and the position the material would be in if there was no indent. This is shown as the distance "d" in FIG. 2.

The position of the second attachment point is determined by reference to the position of a patient's hip. The positions of the first and third attachments points are determined by reference to the patient's condition. The strength of the correctional force applied by the orthotic device may depend in part on the resilience of the reinforcement panel 40, and in part on the depth of the indent at the first attachment point 51.

Figure 3:
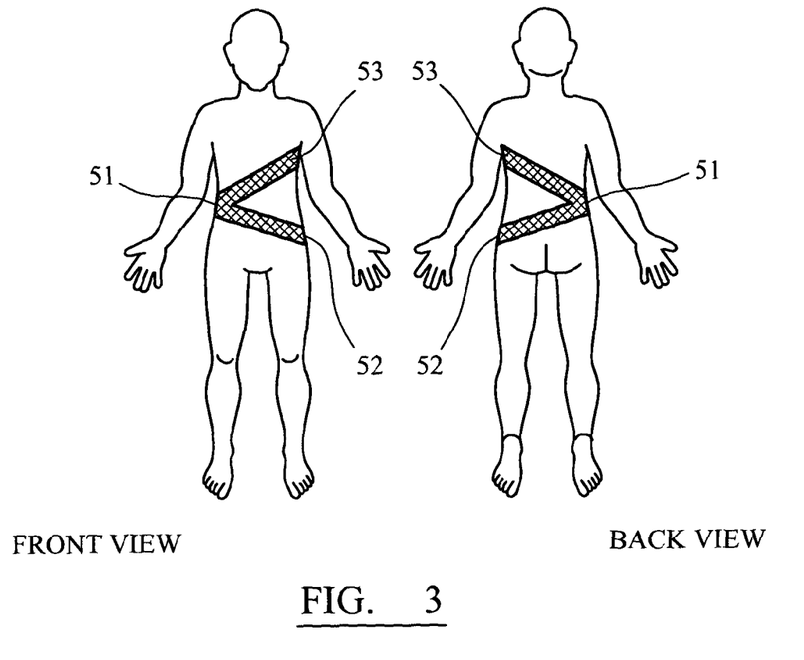
FIG. 3 illustrates front and rear views of a wearer of an orthotic device according to an embodiment of the invention and illustrates the position of translational reinforcement panels.

FIG. 3 is a schematic diagram illustrating the position of the first reinforcement panel 40 on a wearer of the suit. The position of the first attachment point 51, the second attachment point 52, and the third attachment point 53, is shown in both front and rear views. While the second attachment point 52 is preferably fixed with respect to a wearer's hip, the first and third attachment points may vary depending on the wearer's condition.

The body suit of this specific embodiment also comprises a second spinal de-rotation reinforcement panel 90. This second reinforcement panel originates at a first end 97 located at an anterior portion of the torso section adjacent to the right shoulder. The panel then extends over the shoulder and downwards beneath the right armpit 91, 99 of the torso section. The panel 90 then extends diagonally downwards across the front of the body-suit, to a second end 92 located at a left hip portion of the torso section. The second reinforcement panel 90 lies beneath the first reinforcement panel 40 in this embodiment.

The second reinforcement panel 90 generates a strong compressive force to the right side of the wearer's torso. The suit incorporates a pressure relief panel 95 at a left shoulder of the torso section to compensate for this pressure. The pressure relief panel 95 is an adjustable Velcro® fastened flap. When donning the suit, the pressure relief panel is the final component to be fastened.

Figure 4:
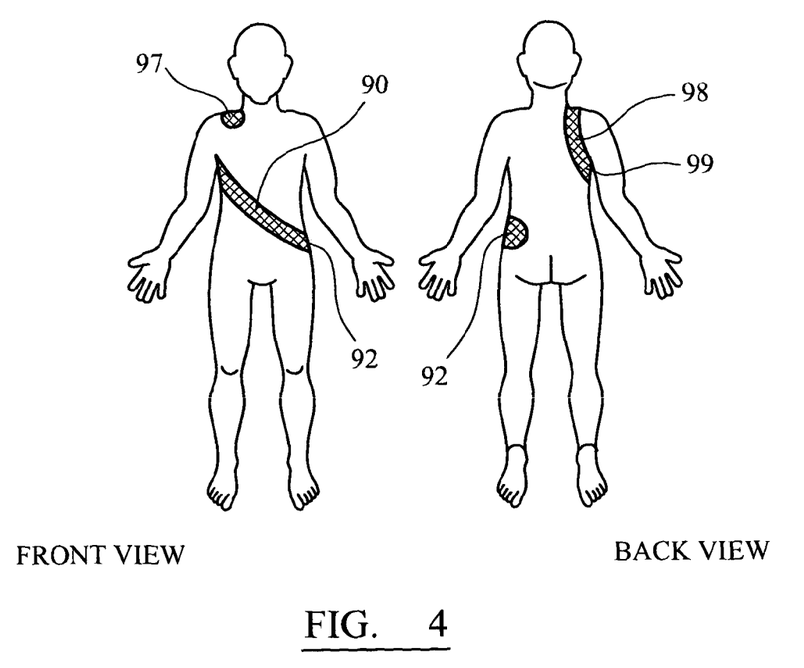
FIG. 4 illustrates front and rear views of a wearer of an orthotic device according to an embodiment of the invention and illustrates the position of spinal de-rotational reinforcement panels.

FIG. 4 is a schematic illustration showing in front and rear views the position of the second reinforcement panel (spinal de-rotation panel) on a wearer when the suit is worn. The panel 90 can be seen to extend from a first end 97 on an anterior portion of the wearer's shoulder, downwardly over the wearer's right shoulder blade 98 and underneath the right armpit 99. The panel 90 then extends diagonally downwards across the wearer's chest and terminates at a second end 92 located at the anterior superior iliac spine.

When the body-suit 10 is worn, the suit conforms to the wearer's body. At the first attachment point 51 the suit needs to stretch in order to eliminate the indent and conform to the wearer's body. The first reinforcement panel 40 is, therefore, stretched and elastic forces are generated between the first attachment point and the second attachment point, and between the first attachment point and the third attachment point. These forces are illustrated in FIG. 1 as double-headed arrows extending along the upper and lower portions 43, 42 of the first reinforcement panel 40. The result of the forces generated in the upper and lower portions 43, 42 of the first reinforcement panel 40 is that a force is generated that urges the wearer's torso from right to left as indicated by arrow 110 in FIG. 1. The second reinforcement panel 90 simultaneously acts to compress the spine and prevent thoracic spine rotation.

In alternative embodiments, the suit may have an arm section, for covering a wearer's arm, on the same side as the first end of the second reinforcement panel. For example, if an arm section were attached to the suit of FIG. 1 it would be a right arm section. An arm section may act to prevent the shoulder from coming forward.

To treat a scoliosis sufferer, the first attachment point would be provided on the convex side of the scoliotic curve, so that the force provided by the panel urges the spine towards a more normal curvature. The vertical position of the first attachment point and the vertical position of the second attachment point would be determined by reference to x-rays showing the abnormal curvature of the spine.

For example, the apex of the first reinforcement panel (the first attachment point) may be vertically positioned to apply a force to the rib below the vertebral angle lower "null" point of the scoliotic curve. The pressure from the reinforcement is thus applied, via the rib, to the vertebra at the lower "null" point of the scoliotic curve. The first attachment point should not be positioned higher than this, as pressure applied incorrectly may have detrimental results for the patient.

The vertical position of the third attachment point may likewise be determined from the patient's x-rays. The third attachment point may, for example, apply pressure to the rib below the vertebral angle upper "null" point of the scoliotic curve.

The magnitude of the corrective force may be tailored by altering the depth of the indent.

The invention claimed is:

1. An orthotic device for donning by a wearer to treat scoliosis, comprising:
   a torso section fabricated from resilient material, configured for conforming to at least a portion of the wearer's torso, and including a front portion, a rear portion, a first side, and a second side, wherein the first side includes a first attachment point and the second side includes a second attachment point and a third attachment point, wherein the torso section has a shape wherein at least one of the first, second, and third attachment points is indented relative to adjacent portions of the respective first and/or second sides such that a circumference of the torso section is reduced at the indent or indents when the torso section is in a non-tensioned condition; and
   a reinforcement configured for applying a force to the wearer's torso to urge a portion of the wearer's spine in a lateral direction to treat scoliosis, the reinforcement comprising a panel of resilient material including two panel portions that are angled relative to each other to form a V-shape, that are attached to the torso section, and that extend across the front portion, the rear portion, or both, of the torso section between the first and second sides, with a first apex end of the V-shaped reinforcement attached to the first attachment point at the first side of the torso section and second and third opposite ends of the reinforcement attached to the second and third attachment points at the second side of the torso section,
   wherein the resilient reinforcement is attached to the first, second, and third attachment points of the torso section with the resilient reinforcement in a non-tensioned condition such that the resilient reinforcement attached to the torso section is stretched automatically and thereby becomes tensioned only when the orthotic device is donned by the wearer and thereby applies the force to the wearer's torso, and
   wherein the indent or indents at the first, second, and/or third attachment points are formed when the torso section and the reinforcement are both in their respective non-tensioned conditions such that the indent or indents are formed by the shape of the torso section in its non-tensioned condition and not due to untensioning of the reinforcement, and
   wherein the reinforcement does not extend over any of the wearer's shoulders when worn.

2. An orthotic device according to claim 1, wherein the material forming the torso section is a lightweight resilient material that can conform to the wearer's body without giving rise to lines of tension or compression in any specific direction, and the reinforcement comprises a different resilient material.

3. An orthotic device according to claim 2, wherein the reinforcement comprises sections of the different resilient material capable of providing a constant force to urge the wearer's torso in a specific direction, the sections of the different resilient material being applied to the torso section in the form of panels or strips of material.

4. An orthotic device according to claim 1, wherein the first attachment point is situated vertically higher than the second attachment point and vertically lower than the third attachment point.

5. An orthotic device according to claim 1, wherein the reinforcement is a first reinforcement, further comprising a second reinforcement, the second reinforcement comprising resilient material stitched to the torso section such that it applies a rotational force that is configured to rotate the torso of the wearer, wherein the second reinforcement has a first end located at the front portion of the torso section adjacent to a shoulder of the torso section, extends over the shoulder and downwards beneath an armpit of the torso section, and further extends diagonally downwards across the front portion of the torso section to a second end located at a hip portion of the torso section.

6. An orthotic device according to claim 1, wherein the magnitude of the force generated by the reinforcement when the device is worn is related to a depth that at least one of the attachment points is indented into the respective side of the torso section.

7. An orthotic device according to claim 1 wherein in use the second attachment point is configured to be located at the wearer's hip on the second side of the torso section, the third attachment point is configured to be located below an arm opening on the second side of the torso section, and the first attachment point is configured to be located between the wearer's hip and an arm opening on the first side of the torso section.

8. A method of making the orthotic device according to claim 1, comprising the steps of:
   determining a vertical position of the first attachment point based on x-rays of the wearer's torso;
   producing the torso section for substantially-conforming to the wearer's body, the torso section being indented at the first attachment point; and
   attaching the reinforcement to the torso section such that the reinforcement is automatically stretched when the device is worn.

9. An orthotic device according to claim 1, wherein the reinforcement is stitched to the torso section along edges of the resilient material of the reinforcement.

10. A method of making an orthotic device according to claim 1, comprising the steps of:
    providing the torso section with the first and second sides having the respective indent or indents at the respective first, second, and/or third attachment points pre-existing in the shape of the torso section when in its non-tensioned condition; and
    attaching the reinforcement to the torso section when the reinforcement is in its non-tensioned condition.

11. An orthotic device according to claim 1, wherein the reinforcement is a first reinforcement, further comprising a second reinforcement, the second reinforcement comprising resilient material attached to the torso section such that it applies a rotational force that is configured to rotate the torso of the wearer, wherein the second reinforcement has a first end located at a rear portion of the torso section adjacent to a shoulder of the torso section, extends over the shoulder and downwards beneath an armpit of the torso section, and further extends diagonally downwards across the rear portion of the torso section to a second end located at a hip portion of the torso section, or wherein the second reinforcement has a first end located at the front portion of the torso section adjacent to the shoulder of the torso section, extends over the shoulder and downwards beneath the armpit of the torso section, and further extends diagonally downwards across the front portion of the torso section to a second end located at the hip portion of the torso section.

12. An orthotic device for donning by a wearer to treat scoliosis, comprising:
    a torso section fabricated from resilient material and configured for conforming to at least a portion of the wearer's torso, wherein the torso section has first and second sides with a first attachment point at the first side and second and third attachment points at the second side, wherein the torso section has a shape with at least one of the first and third attachment points indented relative to adjacent portions of the respective first and/or second sides such that a circumference of the torso section is reduced at the indent or indents, wherein the first attachment point is located vertically higher than the second attachment point and vertically lower than the third attachment point, wherein the second attachment point is not indented relative to adjacent portions of the second side; and
    a reinforcement configured for applying a lateral force to the wearer's torso to urge a portion of the wearer's spine in a lateral direction to treat scoliosis, the reinforcement comprising a panel of resilient material including two panel portions that are angled relative to each other to form a V-shape and that extend across the torso section between the first and second sides, with a first apex end of the V-shaped reinforcement attached to the first attachment point at the first side of the torso section and second and third opposite ends of the V-shaped reinforcement attached to the second and third attachment points at the second side of the torso section,
    wherein the indent or indents are formed when the torso section and the reinforcement are both in a non-tensioned condition such that the indent or indents are not formed due to untensioning of the reinforcement, such that the reinforcement is stretched automatically so that the attachment points are no longer indented relative to adjacent portions of the respective first and/or second sides when the orthotic device is donned by the wearer and thereby applies the lateral force to the wearer's torso, and
    wherein the reinforcement does not extend over any of the wearer's shoulders when worn.

13. An orthotic device according to claim 12, wherein the V-shaped panel portions of the reinforcement each extend across a front portion of the torso section between the first and second sides, and wherein the reinforcement further comprises a rear panel of resilient material including two rear panel portions that are angled relative to each other to form a V-shape and that extend across a rear portion of the torso section between the first and second sides.

14. An orthotic device according to claim 13, wherein the front and rear V-shaped panels of the reinforcement together form two bands that encircle the torso section.

15. An orthotic device according to claim 12 wherein the second attachment point is configured to be located at the wearer's hip on the second side of the torso section and the third attachment point is located below an arm opening on the second side of the torso section, the first attachment point being configured to be located between the wearer's hip and an arm opening on the first side of the torso section.

16. An orthotic device according to claim 12, wherein an upper one of the panel portions of the V-shaped reinforcement extends diagonally across the torso section between the first and third attachment points, and the third attachment point is vertically spaced from the second attachment point on the second side of the torso section and the first attachment point is vertically positioned between the second and third attachment points, the reinforcement being configured to apply the lateral force to urge the wearer's torso in the lateral direction toward the second side of the torso section.

17. An orthotic device according to claim 12, wherein the circumference of the torso section is reduced at the indent or indents by 7.5% to 20%.

18. An orthotic device for donning by a wearer to treat scoliosis, comprising:
    a torso section fabricated from resilient material and configured for conforming to at least a portion of the wearer's torso, wherein the torso section has first and second sides with a first attachment point at the first side and second and third attachment points at the second side, and wherein the torso section has a shape with the first attachment point indented relative to adjacent portions of the first side and with the third attachment point indented relative to adjacent portions of the second side such that a circumference of the torso section is reduced at the indents and thus such that when donned by the wearer the torso section needs to stretch more at the indents than at the adjacent portions to conform to the wearer's torso, wherein the first attachment point is located vertically higher than the second attachment point and vertically lower than the third attachment point, and wherein the second attachment point is not indented relative to adjacent portions of the second side; and a reinforcement configured for applying a lateral force to the wearer's torso to urge a portion of the wearer's spine in a lateral direction to treat scoliosis, the reinforcement comprising a panel of resilient material including two panel portions that are angled relative to each other to form a V-shape and that extend across the torso section between the first and second sides, with a first apex end of the V-shaped reinforcement attached to the first attachment point at the first side of the torso section and second and third opposite ends of the V-shaped reinforcement attached to the second and third attachment points at the second side of the torso section, wherein at least one of the panels of the V-shaped reinforcement extends diagonally across the torso section between the indents of the first and second sides, wherein the indents are formed when the torso section and the reinforcement are both in a non-tensioned condition such that the indents are not formed due to untensioning of the reinforcement, wherein the reinforcement is stretched automatically when the orthotic device is donned by the wearer and thereby applies the lateral force to the wearer's torso, and wherein the reinforcement does not extend over any of the wearer's shoulders when worn.

\* \* \* \* \*